(12) United States Patent
Torrence et al.

(10) Patent No.: US 8,697,908 B2
(45) Date of Patent: Apr. 15, 2014

(54) REMOVAL OF AMINE COMPOUNDS FROM CARBONYLATION PROCESS STREAM CONTAINING CORROSION METAL CONTAMINANTS

(75) Inventors: G. Paull Torrence, League City, TX (US); Brian Hokkanen, Houston, TX (US); Yaw-Hwa Liu, Missouri City, TX (US)

(73) Assignee: Celanese International Corporation, Dallas, TX (US)

( * ) Notice: Subject to any disclaimer, the term of this patent is extended or adjusted under 35 U.S.C. 154(b) by 586 days.

(21) Appl. No.: 13/101,781

(22) Filed: May 5, 2011

(65) Prior Publication Data

US 2012/0283471 A1 Nov. 8, 2012

(51) Int. Cl.
*C07C 51/12* (2006.01)
*C07C 51/47* (2006.01)

(52) U.S. Cl.
USPC .......................... 562/519; 562/517; 562/518

(58) Field of Classification Search
None
See application file for complete search history.

(56) References Cited

U.S. PATENT DOCUMENTS

| | | |
|---|---|---|
| 3,769,329 A | 10/1973 | Paulik |
| 4,007,130 A | 2/1977 | Leach |
| 4,628,041 A | 12/1986 | Smith |
| 4,894,477 A | 1/1990 | Scates |
| 4,908,477 A | 3/1990 | Hartmann |
| 4,994,608 A | 2/1991 | Torrence |
| 5,001,259 A | 3/1991 | Smith |
| 5,026,908 A | 6/1991 | Smith |
| 5,144,068 A | 9/1992 | Smith |
| 5,300,715 A | 4/1994 | Vora |
| 5,466,876 A | 11/1995 | McClarron |
| 5,696,284 A | 12/1997 | Baker |
| 5,731,252 A | 3/1998 | Warner |
| 5,877,347 A | 3/1999 | Ditzel |
| 5,877,348 A | 3/1999 | Ditzel |
| 5,883,295 A | 3/1999 | Sunley |
| 5,917,089 A | 6/1999 | Howard |
| 5,932,764 A | 8/1999 | Morris |
| 5,942,460 A | 8/1999 | Garland |
| 6,106,702 A | 8/2000 | Sohn et al. |
| 6,143,390 A | 11/2000 | Takamiya |
| 6,339,171 B1 | 1/2002 | Singh |
| 6,346,645 B1 | 2/2002 | Kulprathipanja et al. |
| 6,627,770 B1 | 9/2003 | Cheung |
| 6,657,078 B2 | 12/2003 | Scates |
| 7,005,541 B2 | 2/2006 | Cheung |
| 7,223,886 B2 | 5/2007 | Scates |
| 2005/0197513 A1 | 9/2005 | Trueba |
| 2006/0247466 A1 | 11/2006 | Zinobile |
| 2006/0293537 A1 | 12/2006 | Trueba |
| 2008/0287706 A1 | 11/2008 | Powell |
| 2008/0293966 A1 | 11/2008 | Scates |
| 2009/0107833 A1 | 4/2009 | Warner |
| 2009/0270651 A1 | 10/2009 | Zinobile |

FOREIGN PATENT DOCUMENTS

| | | |
|---|---|---|
| DE | 102007030440 | 1/2009 |
| EP | 0849248 | 6/1998 |
| GB | 2334955 | 9/1999 |

OTHER PUBLICATIONS

Bodis, J., "Carbonylation of Methanol over Supported Rhodium Catalysts," in Situ Spectrosopy of Monomer and Polymer Synthesis, pp. 187-205.
Collins et al., "Process for removal of traces of amines from refined methanol using ion-exchange resins," Chemistry and Industry, Feb. 19, 1972, pp. 173-174.
English language abstract for DE 102007030440 A1.
Jones, J. H., "The Cativa Process for the Manufacture of Acetic Acid", Platinum Metals Review, 44 (3), pp. 94-105 (2000).
International Search Report and Written Opinion for PCT/US2012/036278 mailed Sep. 5, 2012.
International Search Report and Written Opinion for PCT/US2012/036283 mailed Sep. 5, 2012.
International Preliminary Report on Patentability for PCT/US2012/036278 mailed Nov. 14, 2013.

*Primary Examiner* — Yevegeny Valenrod (57) ABSTRACT

A process for removing amine compounds from a process stream derived from a carbonylation process. The amine compounds may be present as iodide salts. The process stream also contains corrosion metal contaminants. The amine compounds are removed by mixing a portion of the process stream a slipstream to form an aqueous stream having a water concentration of greater than 50 wt. %. The aqueous stream is contacted with an exchange resin to remove amine compounds, as well as corrosion metal contaminants.

20 Claims, 3 Drawing Sheets

REMOVAL OF AMINE COMPOUNDS FROM CARBONYLATION PROCESS STREAM CONTAINING CORROSION METAL CONTAMINANTS

FIELD OF THE INVENTION

The present invention is directed to a method for removing amine compounds from a carbonylation process stream containing corrosion metal contaminants, in particular for removing amine compounds from an aqueous stream using an exchange resin.

BACKGROUND OF THE INVENTION

A widely used and successful commercial process for synthesizing acetic acid involves the catalyzed carbonylation of methanol with carbon monoxide. The catalysts contain rhodium and/or iridium and a halogen promoter, typically methyl iodide. The reaction is conducted by continuously bubbling carbon monoxide through a liquid reaction medium in which the catalyst is dissolved. The reaction medium also comprises methyl acetate, water, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in Jones, J. H. (2002), "*The Cativa™ Process for the Manufacture of Acetic Acid*," Platinum Metals Review, 44 (3): 94-105, the entire content and disclosure of which is hereby incorporated by reference. The reaction solution is withdrawn from the reactor and purified to obtain acetic acid.

During the purification of the reaction solution, several process streams are recycled to the reactor. The recycling of these streams often causes various impurities to build up in the carbonylation reactor. Corrosion metal contaminants, such as compounds containing iron, nickel, molybdenum, chromium, and the like are some examples of these impurities. These corrosion metal contaminants are formed due to the corrosive nature of the reaction solution and/or process streams. The corrosion metal contaminants build up in the carbonylation process streams as the process is operated over extended periods of time. As the corrosion metal contaminants are recycled to the reactor, these contaminants may build up in sufficient quantities, which can interfere with the carbonylation reaction and/or accelerate competing reactions such as the water-gas shift reaction or methane formation. The presence of these corrosion metal contaminants can have adverse effects on the process, in particular, a consequent loss in yield based on carbon monoxide. Further, corrosion metal contaminants can react with halogen catalyst promoters, which reduces the stability of the catalyst system. The need therefore exists for reducing the amount of corrosion metal contaminant in a carbonylation reaction system.

Several processes have been used to remove corrosion metal contaminants. U.S. Pat. No. 4,007,130 describes contacting a catalyst solution containing metallic corrosion products with an ion exchange resin in its hydrogen form to recover the catalyst solution free of the metal contaminants. U.S. Pat. No. 4,628,041 describes recovering rhodium and iodine values in the manufacture of acetic acid by carbonylation by precipitating the rhodium to separate it from corrosion metal contaminants. U.S. Pat. No. 4,894,477 describes a process that uses strongly acidic ion exchange resins in the lithium form to remove corrosion metal contaminants. U.S. Pat. No. 5,466,876 describes a chelating resin that is selective for the removal of corrosive metals rather than to carbonylation catalyst and co-promoter. U.S. Pat. No. 5,731,252 describes contacting the catalyst solution with an ion exchange resin bed, in the lithium form, and using a sufficient amount of water to decrease the concentration of alkali metal ions to optimize removal of corrosion metal contaminants.

In addition to corrosion metal contaminants, other impurities may be present and/or may tend to build up in the carbonylation process, thus causing adverse effects such as process equipment fouling. These impurities may be difficult to remove with exchange resin beds when corrosion metal contaminants are present since the corrosion metal contaminants tend to bind to exchange resin beds more aggressively than do other impurities.

As will be appreciated by one of skill in the art, there is an incentive to improve existing processes for the production of acetic acid by reducing the amount of impurities.

SUMMARY OF THE INVENTION

In a first embodiment, the present invention is directed to a process for removing amine compounds in a carbonylation process. A carbonylation process stream comprising acetic acid, a metal compound of a carbonylation catalyst, and impurities, the impurities comprising at least one amine compound and at least one corrosion metal contaminant is provided. The process comprises mixing a slipstream with a portion of the process stream to form an aqueous stream having a water concentration of greater than 50 wt. %, contacting the aqueous stream with an exchange resin, and withdrawing a purified process stream from the exchange resin, wherein the purified process stream comprises a reduced amine content.

In a second embodiment, the present invention is directed to a process for removing amine compounds in a carbonylation process. The carbonylation process comprises reacting carbon monoxide with at least one reactant in a reactor containing a reaction medium to produce a reaction solution comprising acetic acid. The at least one reactant is selected from the group consisting of methanol, methyl acetate, methyl formate, dimethyl ether and mixtures thereof. The reaction medium comprises water, acetic acid, methyl acetate, methyl iodide, and a catalyst. The reaction solution is withdrawn and fed to flasher that yields a vapor crude product stream and a carbonylation process stream. The carbonylation process stream comprises acetic acid, a metal compound of a carbonylation catalyst, and impurities, the impurities comprising at least one amine compound and at least one corrosion metal contaminant. To remove the impurities, the carbonylation process stream is mixed a slipstream to form an aqueous stream having a water concentration of greater than 50 wt. % and contacted with an exchange resin. The withdrawn purified process stream from the exchange resin comprises a reduced amine content.

In a third embodiment, the present invention is directed to a process for removing amine compounds in a carbonylation process, the process comprising the steps of contacting at least one reactant composition, comprising (i) a reactant selected from the group consisting of methanol, methyl acetate, methyl formate, dimethyl ether and mixtures thereof and (ii) an amine, with an exchange resin to produce a purified reactant feed stream having a reduced amine content; reacting carbon monoxide with the purified reactant feed stream in a reactor containing a reaction medium to produce a reaction solution comprising acetic acid, and wherein the reaction medium comprises water, acetic acid, methyl acetate, methyl iodide, and a catalyst; and withdrawing a reaction solution from the reactor, wherein the reaction solution is substantially free of amine compounds.

BRIEF DESCRIPTION OF DRAWINGS

The invention is described in detail below with reference to the appended drawings, wherein like numerals designate similar parts.

DETAILED DESCRIPTION OF THE INVENTION

The present invention generally relates to acetic acid production by methanol carbonylation under low water conditions. The methanol reactants fed to the carbonylation process may contain, depending on grade, low levels of impurities, including one or more amine compounds. The amine compounds may build up in the carbonylation process and, in particular, in the carbonylation reactor and an accompanying flasher. The amine compounds tend to form inorganic amine salts, and as a result the inorganic iodide concentration will increase in the reactor and/or flasher. As a result the general corrosion increases resulting in additional amounts of corrosion metals. The presence of additional corrosion metals require further processing to maintain a low concentration of corrosion metals in the reactor and/or flasher. Thus, the presence of amine compounds presents operability issues which may be difficult to control and may lead to inefficient production.

One difficulty in removing amine compounds from a carbonylation process stream is that other impurities, in particular corrosion metal contaminants, tend to dominate impurity removal dynamics. Typically, corrosion metal contaminants are removed from process streams using exchange resins. In some exemplary cases acid solvents, such as acetic acid, may be added to the exchange resin to improve removal efficiency of corrosion metal contaminants. The acidic environment may favor removal of corrosion metal contaminants. However, favoring the removal of corrosive metals contaminants tends to reduce the ability of the exchange resins to remove other impurities such as amine compounds. Previous efforts have focused on removing corrosion metal contaminants using exchange resins, but have failed to recognize the need to remove other impurities such as the aforementioned amine compounds.

In one embodiment, the processes of the present invention overcome the problems associated with the presence of amine compounds and the removal of the amine compounds from carbonylation process streams. In particular, the present invention addresses problems relating to removal of amine compounds from one or more carbonylation process streams that also contains corrosion metal contaminants. Generally, process streams that contain corrosion metal contaminants and amine compounds are acidic. The typical acidic conditions in an exchange resin favor binding of the corrosion metal contaminants over amine compounds. Thus, the exchange resins would be ineffective in removing amine compounds in an acidic environment. Embodiments of the present invention reduce the acidity within the exchange resin, by mixing the process stream, containing corrosion metal contaminants and amine compounds, with a slipstream to form an aqueous stream having a water concentration of greater than 50 wt. %, e.g., greater than 60 wt. %, greater than 75 wt. % or greater than 85 wt. %. In terms of ranges the aqueous stream may have a water concentration from 50 wt. % to 90 wt. %, e.g., from greater than 50 wt. % to 85 wt. % or from 60 wt. % to 85 wt. %. The aqueous stream may create a weakly acidic environment, i.e. pH of above about 4.5, or a non-acidic environment in the exchange resin. The water concentration of the aqueous stream may be controlled by mixing a slipstream with the process stream, or directly feeding to the exchange resin, to dilute the process stream containing corrosion metal contaminants and amine compounds. Multiple slipstreams may be mixed with the process stream, provided that the aqueous stream has a high water concentration. Using the aqueous stream, the amine compounds removal may be improved, even in the presence of corrosion metal contaminants.

The slipstream may comprise methanol, water, methyl acetate, methyl iodide and mixtures thereof. Preferably the slipstream comprises water and minor amounts of organics. Also, the slipstream may comprise acetic acid, e.g., amounts less than about 20 wt. %, e.g., less than 10 wt. % or less than 5 wt. %. In one embodiment, the slipstream may be a dilute acetic acid stream. The slipstream may be obtained from one or more of the process stream within the system. In addition, the slipstream, in some embodiments, may be obtained from a portion of the reactant feed stream. The slipstream may be added to the process stream before contacting the exchange resin or may be added directly to the exchange resin.

In embodiments of the present invention, the term process stream refers to any stream separated during purification that is retained in the carbonylation process. Generally waste streams that are purged or the resultant acetic acid product stream are not referred to as process streams. The process stream(s) may be recycled, directly or indirectly, to the carbonylation reactor. In one embodiment, one or more process stream may be treated in exchange resin to remove corrosion metal contaminants and amine compounds. Also, some process stream(s) may be used as slipstream(s) to form the aqueous stream that contacts the exchange resin. In these cases, the process stream used to form the aqueous stream is different from the process stream treated via the exchange resin.

Figure 1:
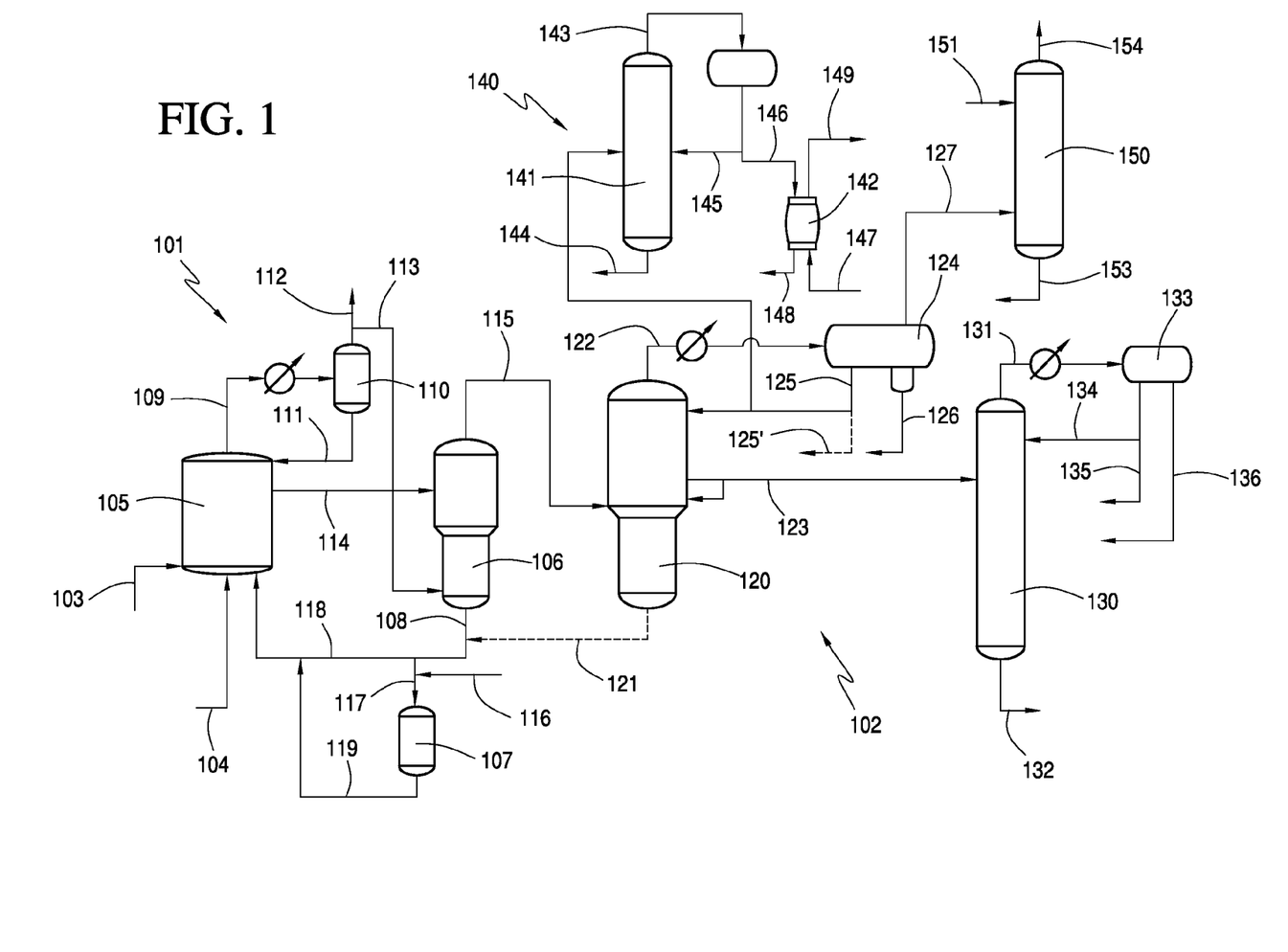
FIG. 1 illustrates a carbonylation process having an exchange resin according to an embodiment of the present invention.

Corrosion metal contaminants, in particular, iron, nickel, chromium and molybdenum may be present in any of the process streams of the carbonylation process. In general, these corrosion metal contaminants have an adverse effect on the acetic acid production rate and the overall stability of the process. Accordingly, in accordance with the present invention, an ion exchange resin is placed within the carbonylation process to remove these corrosion metal contaminants, as well as amine compounds, from the process streams. In FIG. 1, catalyst solution process stream 108 is withdrawn from the base of flasher 106, and a portion thereof is passed through exchange resin bed 107 containing the exchange resin. The exiting stream is recycled via line 119 to reactor 105. It should be understood, that any of the process streams can be treated via the ion exchange resin to remove amine compounds and/or metal contaminants therefrom. Process stream 108 should be at a temperature, such as less than 120° C., that does not deactivate the resin. If necessary process stream 108 may be cooled.

The present invention may be applied in any suitable methanol carbonylation process. Exemplary carbonylation processes that may be used with embodiments of the present invention include those described in U.S. Pat. Nos. 7,223,886, 7,005,541, 6,657,078, 6,339,171, 5,731,252, 5,144,068, 5,026,908, 5,001,259, and 4,994,608, and U.S. Pub. Nos. 2008/0287706, 2008/0293966, 2009/0107833, and 2009/0270651, the disclosures of which are hereby incorporated by reference. The exemplary carbonylation system depicted herein may also include further systems and components that may be used with embodiments of the present invention include those described in these patents. It should be understood that the carbonylation system shown in the figures is exemplary and other components may be used with the scope of the present invention. The methanol carbonylation process may comprise a carbonylation section and a purification section. The embodiments of the present invention are not limited by the configuration of the carbonylation or purification sections. Thus, any suitable purification section may be used in combination with any of the embodiments of the present invention.

Exemplary carbonylation section 101 and purification section 102 are shown in FIG. 1. Carbonylation section 101 comprises carbon monoxide feed stream 103, reactant feed stream 104, reactor 105, flasher 106, and exchange resin bed 107, which comprises exchange resin. Carbon monoxide is fed via stream 103 to a lower portion of reactor 105. Other reactants are similarly fed via stream 104. Reactant feed stream 104 supplies to reactor 105 at least one reactant selected from the group consisting of methanol, methanol derivatives, such as methyl acetate, methyl formate, dimethyl ether, and/or mixtures thereof. In preferred embodiments, reactant feed stream 104 supplies methanol and methyl acetate. Optionally, reactant feed stream 104 may be connected to one or more vessels (not shown) that store fresh reactants for the carbonylation process. In addition, there may be a methyl iodide storage vessel (not shown) and/or catalyst vessel (not shown) connected to reactor 105 for supplying fresh methyl iodide and catalyst as needed to maintain reaction conditions. In other embodiments, all or some of the methanol and/or methanol derivatives supplied to reactor 105 may be in the form of scrubbed methanol from another location in the system or as a product or by-product of another system.

One or more process streams from carbonylation section 101 may be recycled to reactor 105. In some embodiments, recycle feed streams comprising the reaction medium components, e.g., residual/entrained catalyst, or acetic acid, are directed to the reactor. Preferably, there are multiple process streams that are recycled and fed, in combination or separately, to reactor 105. For example, one or more process streams from purification section 102 may be fed to reactor 105. Preferably, the recycled process streams are introduced in the lower portion of reactor 105.

In certain embodiments of the invention, reactant feed stream 104 comprises methanol and/or methanol derivatives. Suitable methanol derivatives include methyl acetate, dimethyl ether, methyl formate, and mixtures thereof. In one embodiment, a mixture of methanol and methanol derivatives is used as a reactant in the process of the present invention. Preferably, methanol and/or methyl acetate are used as reactants. At least some of the methanol and/or methanol derivatives thereof will be converted to, and hence be present as, methyl acetate in the reaction medium by reaction with acetic acid product or solvent. The concentration of methyl acetate in the reaction medium is preferably in the range from 0.5 wt. % to 70 wt. %, e.g., from 0.5 wt. % to 50 wt. %, or from 1 wt. % to 35 wt. %, of the total weight of the reaction medium.

In embodiments of the present invention, methanol fed to the carbonylation reaction, e.g., lower grades of methanol, may contain one or more amine compounds. Conventional methanol production processes used higher grades of methanol, which limits the reactant supply sources and increases costs of production. Even higher grades of methanol may contain amine compounds. For example, even 1 wppm of trimethylamine may be sufficient to give methanol a distinct odor. Also, some amine compounds, may be present in the reaction medium. The amine compounds include alkyl amines, aryl amines, heterocyclic amines, and mixtures thereof. Alkyl and aryl amines may include trimethylamine, triethylamine, dimethylethyl amine, diethylmethyl amine, diethylpropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, and benzyldimethylamine. Heterocyclic amines include piperidines, piperazines, pyridines, pyridazines, pyrazines, pyrimidines, triazines, pyrrolidines, pyrroles, pyrazoles, pyrazolines, pyrazolidines, imidazolines, imidazolidines, imidazoles, and triazoles, and substituted heterocyclic compounds thereof. The amine compounds may also comprise diamines, triamines, and tetramines, such as tetramethylhexamethylendiamine, tetramethylethylendiamine, tetramethylpropylendiamine, tetramethylbutylendiamine, pentamethyldiethyltriamine, pentaethyldiethylentriamine, pentamethyldipropylentriamine, tetramethyldiaminomethane, tetrapropyldiaminomethane, hexamethyltriethylentetramine, hexamethyltripropylenetetramine, and diisobutylentriamine. The amine present in the methanol feed streams may vary depending on the grade of the methanol and the type of impurity. In one embodiment, the methanol feed comprises less than 100 wppm amine, based on nitrogen content, e.g., less than 20 wppm or less than 1 wppm. In terms of ranges, the methanol feed stream comprises from 0.1 to 100 wppm amine compounds, based on nitrogen content, e.g., from 0.5 to 50 wppm or from 1 to 20 wppm.

Carbon monoxide feed stream 103 may be essentially pure or may contain small amounts of inerts and impurities such as carbon dioxide, methane, nitrogen, hydrogen, noble gases, water and $C_1$ to $C_4$ paraffinic hydrocarbons. The presence of hydrogen in the carbon monoxide and generated in situ by the water gas shift reaction is preferably kept low (e.g., less than 1 bar partial pressure or less than 0.5 bar partial pressure), as its presence may result in the formation of hydrogenation products. The partial pressure of carbon monoxide in the reaction is preferably in the range from 1 bar to 70 bar, e.g., from 1 bar to 35 bar, or from 1 bar to 15 bar.

In some embodiments of the invention, within reactor 105, methanol is reacted with carbon monoxide in a homogeneous catalytic reaction system comprising a reaction solvent, methanol and/or methanol derivatives, a Group VIII catalyst, at least a finite concentration of water and optionally an iodide salt.

Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]^-$ anion, as is well known in the art. Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding rhodium catalysis and iodide salt generation, see U.S. Pat. Nos. 5,001,259, 5,026,908 and 5,144,068, the entireties of which are hereby incorporated by reference.

When an iridium catalyst is used, the iridium catalyst may comprise any iridium-containing compound that is soluble in the reaction medium. The iridium catalyst may be added to the reaction medium for the carbonylation reaction in any suitable form that dissolves in the reaction medium or is convertible to a soluble form. Examples of suitable iridium-containing compounds that may be added to the reaction medium include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)^-_2Br_2]^-H+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$ and hexachloroiridic acid $[H_2IrCl_6]$. Chloride-free complexes of iridium such as acetates, oxalates and acetoacetates are usually employed as starting materials. The iridium catalyst concentration in the reaction medium is generally in the range of 100 to 6000 wppm. The carbonylation of methanol utilizing iridium catalyst is well known and is generally described in U.S. Pat. Nos. 5,942,460, 5,932,764, 5,883,295, 5,877,348, 5,877,347 and 5,696,284, the entireties of which are hereby incorporated by reference.

Other promoters and co-promoters may be used as part of the catalytic system of the present invention, as described in EP0849248, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the reaction medium and/or any liquid process streams recycled to the reactor from the purification and acetic acid recovery stage. When used, the promoter is suitably present in the reaction medium at a molar ratio of promoter to metal catalyst of 0.5:1 to 15:1, preferably 2:1 to 10:1, more preferably 2:1 to 7.5:1. A suitable promoter concentration is 400 to 5000 wppm.

A halogen co-catalyst/promoter is generally used in combination with the Group VIII metal catalyst component. Methyl iodide is a preferred as the halogen promoter. Preferably, the concentration of halogen promoter in the reaction medium is in the range 1 wt. % to 50 wt. %, and preferably 2 wt. % to 30 wt. %.

The halogen promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Water may be formed in situ in the reaction medium, for example, by the esterification reaction between methanol reactant and acetic acid product. In some embodiments, water is introduced to reactor 105 together with or separately from other components of the reaction medium Water may be separated from the other components of reaction composition withdrawn from reactor 105 and may be recycled in controlled amounts to maintain the required concentration of water in the reaction medium. Preferably, the concentration of water maintained in the reaction medium is in the range from 0.1 wt. % to 16 wt. %, e.g., from 1 wt. % to 14 wt. %, or from 1 wt. % to 3 wt. % of the total weight of the reaction composition.

In accordance with a preferred carbonylation process of the present invention, the desired reaction rates are obtained even at low water concentrations by maintaining, in the reaction medium, an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In reactor 105 the reaction medium is maintained, preferably automatically, at a predetermined level. This predetermined level may remain substantially constant during normal operation. Into reactor 105, methanol, carbon monoxide, and sufficient water may be continuously introduced as needed to maintain at least a finite concentration of water in the reaction medium. In some embodiments, carbon monoxide is continuously introduced into reactor 105. Carbon monoxide feed 103 is introduced at a rate sufficient to maintain the desired total reactor pressure. The temperature of reactor 105 may be controlled using heat exchangers in a pump around loop.

Acetic acid is typically manufactured in a liquid phase reaction at a temperature from about 160° C. to about 220° C. and a total pressure from about 20 bar to about 50 bar. In some embodiments of the invention, reactor 105 is operated at a temperature from 150° C. to 250° C., e.g., from 155° C. to 235° C., or from 160° C. to 220° C. The pressure of the carbonylation reaction is preferably from 10 to 200 bar, more preferably 10 to 100 bar and most preferably 15 to 50 bar.

A gaseous purge stream 109 may be vented from reactor 105 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Gaseous purge stream 109 may be scrubbed with acetic acid and/or methanol in recovery unit 110 to recover low boiling point components. The gaseous purge stream 109 may be partially condensed and the non-condensable portion from recovery unit 110 may return low boiling point components to the top of reactor 105 via stream 111. The non-condensable portion may comprise methyl acetate, water, and/or methyl iodide. Carbon monoxide in the gaseous purge stream may be vented in line 112 or fed via line 113 to base of flasher 106 to enhance rhodium stability.

Carbonylation product is drawn off from carbonylation reactor 105 at a rate sufficient to maintain a constant level therein and is provided to flasher 106 via stream 114. In flasher 106, the carbonylation product is separated in a flash separation step with or without the addition of heat to obtain a crude product stream 115 comprising acetic acid, and a liquid process stream 108, comprising a catalyst-containing solution. Generally amine compounds are concentrated in liquid process stream 108 in the bottom of flasher 106 and substantially no amine compounds are carried over in crude product stream 115.

The catalyst-containing solution predominantly contains acetic acid, a metal compound of a carbonylation catalyst, e.g., a metal complex of rhodium and/or iridium, and the iodide salt, along with lesser quantities of methyl acetate, methyl iodide, and water. In addition, the catalyst-containing solution may contain minor amounts of corrosion metal contaminants, such as compounds containing iron, nickel, chromium, molybdenum, and the like. In one embodiment, process stream 108 comprises corrosion metal contaminants in an amount from 0.025 wt. % to 1.0 wt. %, based on metal content, e.g., from 0.025 wt. % to 0.5 wt. % or from 0.025 to 0.1 wt. %. The catalyst-containing solution may also contain minor amounts of amine compounds. In one embodiment, process stream 108 comprises amine compounds in an amount from 0.001 wt. % to 1.0 wt. % based on nitrogen content, e.g., from 0.01 to 0.5 wt. % or from 0.05 wt. % to 0.3 wt. %. In process stream 108, the molar ratio of nitrogen in the amine to metal in the corrosion metal contaminants may be greater than 3:1, e.g., greater than 5:1 or greater than 10:1.

Process stream 108 may be initially combined with optional stream 121 obtained from the bottoms of light ends column 120 in purification section 102, prior to being fed to exchange resin bed 107. The bottoms of light ends column 120 in stream 121 may comprise acetic acid, a metal compound of a carbonylation catalyst, and impurities, such as the corrosion metal contaminants. A portion of process stream 108 may be returned to reactor 105 via line 118, thus bypassing exchange resin bed 107. Depending on the reaction conditions, the amount of process stream 108 directed to exchange resin bed 107 may be from 0.1 to 10% of the total mass flow of process stream 108, and more preferably about 1%. Depending on the size of the resin bed 107, increase flows from process stream 108 may pass through resin bed 107. The portion of process stream 108 directed to exchange resin bed 107 is mixed with slipstream 116 to form aqueous stream 117. Aqueous stream 117 has a water concentration of greater than 50 wt. %, e.g., greater than 60 wt. %, greater than 75 wt. % or greater than 85 wt. %, and creates a weakly acidic or non-acidic environment in exchange resin bed 107. In terms of ranges aqueous stream 117 may have a water concentration from 50 wt. % to 90 wt. %, e.g., from greater than 50 wt. % to 85 wt. % or from 60 wt. % to 85 wt. %. Slipstream 116 may be mixed continuously or as need to dilute process stream 108. In other embodiments, slipstream 116 may be added directly to exchange resin bed 107.

The resins useful for removing amine compounds, as well as corrosion metal contaminants, from the process streams according to the present invention may include cation exchange resins either of the strong-acid or the weak-acid type. Both strong- and weak-acid type resins are readily available as commercial products. The weak-acid cation exchange resins are mostly copolymers of acrylic or methacrylic acids or esters or the corresponding nitriles, but a few of those marketed are phenolic resins. Preferably, strong-acid cation exchange resins are utilized. Strong-acid cation exchange resins predominantly comprise sulfonated styrene-divinyl-benzene copolymers although some of the available resins of this type are phenol-formaldehyde condensation polymers. Amberlyst™ 15 (Dow) and Purolite™ CT275 (The Purolite Company) are exemplary commercial resins. Suitable resins may have a cation that corresponds to the cation employed in the halogen promoter. For purposes of illustrating the present invention, a cation exchange resin in its lithium form may be employed, such as those described in U.S. Pat. No. 5,731,252, the disclosure of which is hereby incorporated by reference.

Either gel type resin or the macroreticular type resin are suitable but the latter is preferred since organic components are present in the catalyst solutions being treated. Macroreticular resins are commonly employed in the catalytic art and require minimal water to maintain their swelling properties.

Contacting the catalyst-containing solution having corrosion metal contaminants and amine compounds with the resin may be performed in a stirred vessel wherein the resin is slurried with the catalyst solution with good agitation and the catalyst solution is then recovered by decantation, filtration, centrifuging, etc. However, treatment of the catalyst solutions is usually achieved by passing the catalyst-containing solution through a fixed-bed column of the resin. The catalyst regeneration can be carried out as a batch, semi-continuous or continuous operation either with manual or automatic control employing methods and techniques well known in the art of ion-exchange.

The ion exchange treatment may be performed at temperatures ranging from 0° C. to 120° C., e.g. from 20° C. to 90° C. Lower or higher temperatures are limited only by the stability of the resin to be employed. Chromium removal may be more efficient at the higher temperatures. At the higher temperatures, a nitrogen or CO purge is desirable. If temperatures above the boiling point of the catalyst solutions are employed, then operation under pressure may be required to maintain the solution in the liquid phase. However, pressure is not a critical variable. Generally, atmospheric pressure or a pressure slightly above atmospheric is employed but superatmospheric or subatmospheric pressures can be used if desired.

The rate of flow of process stream 108 through exchange resin bed 107 during removal of amine compounds and corrosive metals, in general, may vary from about 1 to about 50 bed volumes per hour, e.g. from about 1 to about 35 bed volumes per hour or more preferably from about 1 to about 25 bed volumes per hour. Depending on the resin and flow rate, higher bed volumes may be possible. For purposes of the present invention, higher bed volumes, e.g., greater than 20 bed volumes per hour, and short residence time in exchange resin bed 107 may also advantageously favor removal of amine compounds.

Slipstream 116 may comprise methanol, water, methyl acetate, methyl iodide, acetic acid and mixtures thereof. Slipstream 116 may be obtained from outside of the carbonylation system. Preferably slipstream 116 is supplied by one or more of the other process streams from purification section 102 or reactant feed line 104. There are several available process streams to source slipstream 116. Examples of slipstream sources include, but are not limited to, light phase 125', heavy phase 126, residue 144 from PRS 140, raffinate 148 from PRS 140, low-boiling point process stream 153 from vent scrubber 150, light phase 135, heavy phase 136, and combinations thereof. Preferable slipstreams may comprise dilute acetic acid such as light phase 125' and light phase 135, which may be combined in part or whole with other streams.

In one embodiment reactant feed line 104 may be used as slipstream 116. When reactant feed line 104 contains methanol there may be amine compounds as discussed above. Mixing a portion of reactant feed line 104 with process stream 108 may also reduce the amine compounds in reactant feed line 104 prior to being fed to reactor 105. Optionally, the entire reactant feed line 104 may be fed as a slipstream 116 to form the aqueous stream 117.

Resin bed 107 produces an outflow stream 119 comprising a purified process stream comprising a reduced amine content. Outflow stream 119 is preferably returned to reactor 105. In one embodiment, outflow stream 119 contains less corrosion metal contaminants and amine compounds than aqueous stream 117 fed to resin bed 107. Higher water concentrations of the aqueous stream 117 tend to favor increase removal of corrosive metal contaminants and amine compounds. Preferably, outflow stream 119 has a reduced total corrosion metal and amine content. The reduced corrosion metal content may be less than 1 wppm based on total weight of outflow stream 119. Preferably outflow stream 119 is substantially free of corrosion metal contaminants. The reduced amine content may be less than 1 wppm based on total weight of outflow stream 119. In preferred embodiments, outflow stream 119 is substantially free of amine compounds.

After contacting the bed with process stream 108, washing or rinsing of the resin bed with water or the carbonylation product from the process from which the catalyst being treated is derived, such as acetic acid, is essential for removing all the rhodium from the resin bed. The rinsing or washing is effected at similar flow rates as in the removal step.

After the resin has become exhausted, i.e., when the metal contaminants are breaking through into the effluent, the resin can be regenerated by passing therethrough a solution of organic salts; for illustrative purposes, preferably lithium salts. Generally, the lithium salt used in the regenerating cycle has a concentration in the range from about 1 wt. % to about 20 wt. %. Quantities employed and procedures are those well established in the art and recommended by the resin manufacturers. Aqueous lithium acetate is preferred as a regenerating agent since the acetate anion is employed in the reaction system and is readily available for use. A further advantage is that its use eliminates the rinsing step normally required after the regeneration process when other regenerates are employed. To maximize corrosion metal regeneration capacity and to maximize resin bed column performance at relatively high concentrations of lithium acetate, the lithium acetate regeneration solution should contain some acetic acid, or product being produced, to avoid the formation of any insoluble corrosion metal compounds during the regeneration cycle. Precipitation of these compounds during the regeneration cycle could reduce the regeneration performance of the column and also cause plugging of the resin bed. Typically, acetic acid concentrations from about 0.1 to about 95 wt. % can be used, with acetic acid concentrations from about 0.1 to 20 wt. % being preferred.

The ion-exchange operation can be cyclic where more than one resin is available for use. As the resin becomes exhausted in one resin bed, the slip stream of catalyst solution can be diverted to a fresh bed while the exhausted bed is subjected to regeneration.

Crude product stream 115 comprises acetic acid, methyl iodide, methyl acetate, water, alkanes and permanganate reducing compounds (PRC's). Crude product stream 115, as well as subsequent derivative streams, may contain corrosion metal contaminants that form downstream of flasher 106. Crude product stream 115 contains substantially no amine compounds.

Returning to the crude acetic acid product, crude product stream 115 from flasher 106 is directed to purification section 102. In one exemplary embodiment, purification section 102 preferably comprises a light ends column 120, a drying column 130, PRC removal system (PRS) 140, and vent scrubber 150. Suitable purification sections may also comprise additional guard beds and/or heavy ends columns.

In one embodiment, light ends column 120 yields a low-boiling overhead vapor stream 122, a product side stream 123, and an optional bottoms stream 121. The temperature at the base of the light ends column 120, i.e., temperature of the optional exiting bottoms stream 121, preferably is from 120° C. to 170° C. In addition, the temperature at the top of the light ends column, i.e., temperature of low-boiling overhead vapor stream 122, preferably is from 100° C. to 145° C.

Low-boiling overhead vapor stream 122 may comprise methyl iodide, methyl acetate, water, PRC's, acetic acid, alkanes, and dissolved gases. As shown, low-boiling overhead vapor stream 122 preferably is condensed and directed to an overhead phase separation unit, as shown by overhead decanter 124. Conditions are desirably maintained such that the condensed low-boiling overhead vapor stream 122, once in decanter 124, will separate into a light phase and a heavy phase. The light phase and heavy phase, are withdrawn via lines 125 and 126, respectively, and these streams are process streams.

Light phase stream 125 preferably comprises water, acetic acid, and PRC's, as well as methyl iodide and methyl acetate. As shown in FIG. 1, light phase stream 125 may be refluxed to light ends column 120. A portion of light phase stream 125 may also be separated and processed in a PRS 140 to remove PRC's. PRC's may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof.

Optionally, a portion of light phase stream 125 may also be returned to reaction section 101 via stream 125'. When returned to reaction section 101, light phase stream 125' may be fed to exchange resin bed 107 as slipstream 116. Heavy phase stream 126 from decanter 124 can be conveniently recirculated, either directly or indirectly, to reactor 105. A portion of heavy phase stream 126 may be fed as slipstream 116 to exchange resin bed 107 and preferably in combination with light phase stream 125'. Optionally, a portion of the heavy phase 126 may be recirculated to reactor 105, with a slip stream (not shown), generally a small amount, e.g., from 5 to 40 vol. %, or from 5 to 20 vol. %, of heavy phase 126 being directed to PRS 140.

PRS 140 comprises a column 141 and extractor 142. Column 141 yields a vapor overhead stream 143 and a bottom process stream 144. Bottom process stream 144 comprises water, methyl acetate, methanol and mixtures thereof. A portion of bottom process stream 144 may be fed as slipstream 116 to exchange resin bed 107. Overhead stream 143 may be enriched in at least one PRC and may also contain methyl iodide. Overhead stream 143 is condensed and collected in accumulator. A portion of condensed overhead stream 143 can be refluxed back to column 141 via stream 145. The remaining portion of condensed overhead stream is fed to extractor 142 via stream 146. In one embodiment, stream 146 may contain methanol and methyl acetate at a combined concentration of less than about 10 wt. %, e.g., less than about 5 wt. %, less than about 2 wt. %, or less than about 1.5 wt. %. Also stream 146 may contain less than about 3 wt. % acetic acid, e.g., less than about 1 wt. %, or less than about 0.5 wt. %.

Extraction with an aqueous stream 147, such as water, may be either a single stage or multistage extractor and any equipment used to conduct such extractions can be used in the practice of the present invention. Multistage extraction is preferred. For example, extraction can be accomplished by combining stream 146 with aqueous stream 147 and providing the combination successively to a mixer and then a separator. Multiple such combinations of mixer and separator can be operated in series to obtain a multistage extraction. Multistage extraction may be accomplished in a single vessel having a series of trays. The vessel may be equipped with paddle(s) or other mechanisms for agitation to increase extraction efficiency.

The mutual solubility between the two phases in the extraction can increase with temperature. Accordingly, it is desirable that the extraction be conducted at a combination of temperature and pressure such that the extractor contents can be maintained in the liquid state. Moreover, it is desirable to minimize the temperatures to which stream 146 is exposed to minimize the likelihood of polymerization and condensation reactions involving acetaldehyde. Water used in the extraction is desirably from an internal stream so as to maintain water balance within the reaction system. Dimethyl ether (DME) can be introduced to the extraction to improve the separation of methyl iodide in the extraction, i.e., to reduce the loss of methyl iodide into the waste stream 149. The DME can be introduced to the process or formed in situ.

In extractor 142, stream 146 is desirably provided proximate to one end of the vessel with aqueous stream 147 being provided proximate to the other end of the vessel or such other location to obtain a countercurrent flow. A waste stream 149 comprising the at least one PRC, namely acetaldehyde, is extracted by the water. Waste stream 149, in some embodiments, may strip acetaldehyde and recirculate water to the process. Raffinate, notably containing methyl iodide is withdrawn from extractor 142 as a process stream 148. A portion of raffinate 148 may be fed as slipstream 116 to exchange resin bed 107.

PRC removal columns are further described in U.S. Pat. Nos. 6,143,930, 6,339,171, and 7,223,886, and U.S. Pub. Nos. 2005/0197513, 2006/0247466, and 2006/0293537, the disclosures of which are hereby incorporated by reference. An exemplary two-stage distillation PRS comprising one or more extractors is described in U.S. Pat. No. 7,223,886. An exemplary single stage PRS, similar to those shown in FIG. 1, is described in U.S. Pub. No. 2006/0247466.

Product side stream 123 from the light ends column may comprise acetic acid and water. Product side stream 123 preferably is in the liquid phase and is withdrawn from the light ends column 120 at a temperature from 115° C. to 160° C., e.g., from 125° C. to 155° C. A portion of stream 123 may be returned to light ends column 120.

Drying column 130 separates product side stream 123 to yield an overhead stream 131 comprised primarily of water and a dried product stream 132. The dried purified product stream 132 preferably comprises acetic acid in an amount greater than 90 wt. %, e.g., greater than 95 wt. % or greater than 98 wt. %. The temperature at the base of drying column 130, i.e., temperature of the exiting dried purified product stream 132, preferably is from 130° C. to 185° C., 140° C. to 180° C., e.g., from 150° C. to 175° C. The temperature at the top of drying column 130, i.e., temperature of overhead stream 131, preferably is from 110° C. to 150° C., 120° C. to 150° C., e.g., from 130° C. to 145° C. In some embodiments, the pressure in drying column 130 is from 2 bar to 7 bar, e.g., 3 bar to 6 bar, or 4 bar to 5 bar. Optionally, dried purified product stream 132 may be further treated in one or more guard beds (not shown) and/or heavy end columns (not shown) to further remove impurities, such as halides, or heavier acids and/or esters.

Overhead stream 131 of the drying column may be cooled and condensed in an overhead receiver 133 to form a light phase and a heavy phase. A portion of the light phase from receiver 133 may be refluxed to drying column 130 via line 134. The remaining portion of light phase 135 may be a process stream and fed to exchange resin bed 107 as slipstream 116. Heavy phase 136 is also a process stream that may be returned to the reaction section 101. A portion of heavy phase 136 may be fed as slipstream 116 to exchange resin bed 107. The condensed overhead stream 131, either as light phase 135 or heavy phase 136, is preferably used as slipstream 116 because both streams contain relatively high amounts of water.

Non-condensable gases from decanter 124 may be removed by vent stream 127 and treated in vent scrubber 150. A scrubbing solvent 151, preferably chilled to less than 25° C., may be fed to vent scrubber 150 to scrub vent stream 127 of low boiling point components, such as methyl iodide, which are removed as a process stream via line 153. A portion of low boiling point components in line 153 may be fed as slipstream 116 to exchange resin bed 107. Scrubbing solvents include methanol, methyl acetate, dimethyl ether, acetic acid and mixtures thereof. The overheads of recovery unit 150 may exit as purge gas 154 that comprises carbon monoxide and other inert gases.

Although FIG. 1 illustrates processing the catalyst-containing solution in line 108 from flasher 106, other process streams described above may also be treated in one or more exchange resins to remove corrosive metals and/or amine compounds.

Figure 2:
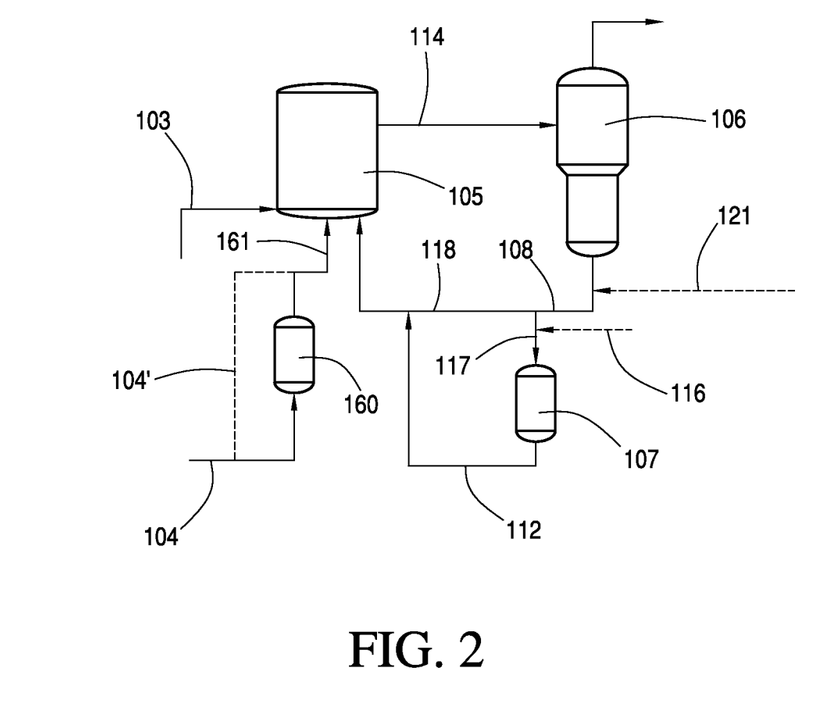
FIG. 2 illustrates a carbonylation section having an exchange resin for the reactant feed stream according to an embodiment of the present invention.

FIG. 1 depicts embodiments in which amine compounds are removed in the presence of corrosion metal contaminants. FIG. 2 shows another embodiment in which amine compounds in the reactant feed stream 104 are initially treated and removed in exchange resin bed 160, which comprises a suitable exchange resin, before being fed to reactor 105. For clarity, the recovery unit 110 and purification section 102 are not illustrated in FIG. 2.

As previously indicated, reactant feed stream 104 may comprise low grades of methanol that contain amine compounds. Exchange resin bed 160 may be similar to the exchange resins described in this application. Typically there are no corrosion metal contaminants in the reactant feed stream 104 and the reactant feed stream 104 is generally non-acidic. A solvent, such as an aqueous slipstream, may be added to exchange resin bed 160. Exchange resin bed 160 produces an outflow 161 that is fed to reactor. The reduced amine content may be less than 1 wppm based on total weight of outflow stream 161 and more preferably outflow stream 161 is substantially free of amine compounds. Advantageously, reaction solution 114 withdrawn from reactor 105 may be substantially free of amine compounds. Thus, no amine compounds in the form of iodide salts build up in flasher 106. Also, exchange resin bed 107 in FIG. 2 may be used to remove corrosion metal contaminants.

Slipstream 116 in FIG. 2 is optional and may contain acetic acid to create an acidic environment to favor removal of corrosion metal contaminants when reaction solution 114 is substantially free of amine compounds. In preferred embodiments, exchange resin bed 160 may be sized to process the entire flow from reactant feed stream. However, it may be necessary to by-pass exchange resin bed 160 via line 104' to maintain reaction conditions. When reactant feed line 104' by-passes exchange resin bed 160, slipstream 116 may be added to create an aqueous stream 117 having a water concentration of greater than 50 wt. %.

One of ordinary skill in the art having the benefit of this disclosure can design and operate the distillation columns described herein to achieve the desired results of the present invention. Such efforts, although possibly time-consuming and complex, would nevertheless be routine for one of ordinary skill in the art having the benefit of this disclosure. Accordingly, the practice of this invention is not necessarily limited to specific characteristic of a particular distillation column or the operation characteristics thereof, such as the total number of stages, the feed point, reflux ratio, feed temperature, reflux temperature, column temperature profile, and the like.

In order that the invention disclosed herein may be more efficiently understood, an example is provided below. It should be understood that these examples are for illustrative purposes only and is not to be construed as limiting the invention in any manner.

EXAMPLES

Resin capacity is measured by making a "flow through" measurement. In these experiments, a glass column (2 cm×50 cm) was charged with 50 mL of sulfonic acid resin (Dow Amberlyst™ 15 or Purolite™ CT-275). The resin was supported using glass wool in the bottom of the column. The resin was loaded in the water wet, hydrogen form and was backwashed with 10 bed volumes of distilled water to remove fines and classify the resin bed prior to use.

Several runs were then performed to evaluate the capacity of the resin for removal of amines in the contaminated resin bed feed. The feed was composed of methanol carbonylation reactor content solution which was diluted into various bulk liquids, such as water, acetic acid, methanol, methyl acetate in a 1:10 weight ratio. The reactor solution contains rhodium, acetic acid, methyl iodide, methyl acetate, water, and the nitrogen containing impurities to be removed by the resin.

Figure 3:
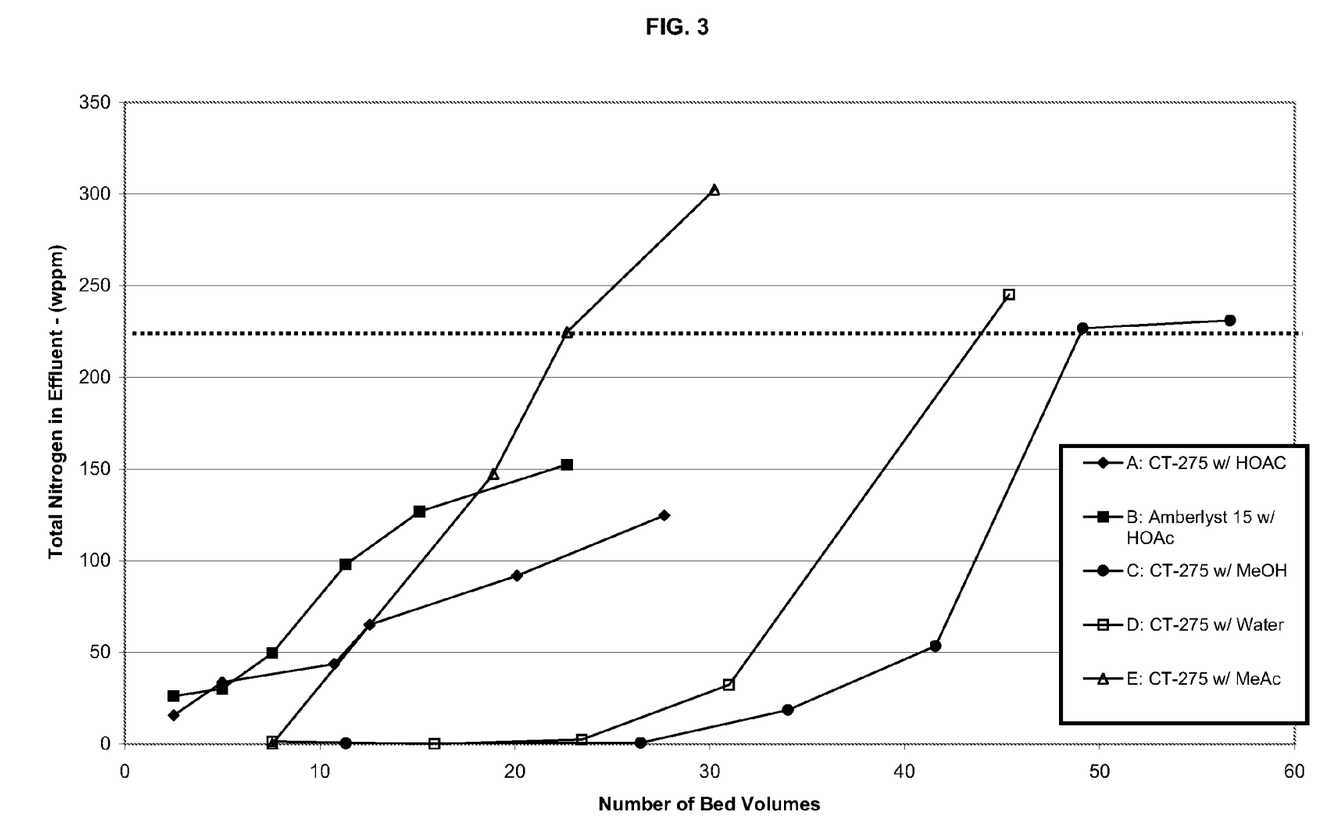
FIG. 3 is a chart comparing resin capacity for different bulk liquids.

The diluted methanol carbonylation reactor solution was passed down flow over the resin bed at a rate of 3.5 grams/minute, or about 4 bed volumes per hour. The column effluent was then collected at various consecutive time intervals, and the effluent sample was analyzed for its total nitrogen content. The results are plotted in FIG. 3 as bed volumes of flow vs. total nitrogen content in the column effluent.

The bulk liquid for Runs A and B was acetic acid. The bulk liquid for Runs C, D, and E was methanol, water, and methyl acetate respectively. Sulfonic acid type resin was used in each of the runs. Run A, C, D, and E used Purolite CT-275 as the resin bed. Run B used Amberlyst 15 as the resin bed.

The capacity of the resin bed to remove nitrogen impurities is defined as the total number of bed volumes of diluted reactor feed material that has passed through the column before the total nitrogen in the bed effluent equals the total nitrogen in the diluted feed material. At this point, the bed cannot remove any more nitrogen containing impurities from the diluted feed material. The resin capacity breakthrough point in these experiments is the point at which the effluent and the feed material equal 225 wppm total nitrogen as represented by the dotted line in FIG. 3. The overall comparative resin capacities for removal of nitrogen impurities is in decreasing order C>D>A, B>E. The breakthrough times for Runs C and D resulted in superior resin capacities for removal of nitrogen containing impurities compared to runs A and B and significantly better than run E. From the series of experiments demonstrated in FIG. 3, the best removal of nitrogen containing impurities from reactor solutions (maximum resin bed capacity) is obtained by diluting an acetic acid stream with methanol and/or water.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art.

Furthermore, those of ordinary skill in the art will appreciate that the foregoing description is by way of example only, and is not intended to limit the invention.

We claim:

1. A process for removing amine compounds in a carbonylation process, the process comprising the steps of:
    providing a carbonylation process stream comprising acetic acid, a metal compound of a carbonylation catalyst, and impurities, the impurities comprising at least one amine compound and at least one corrosion metal contaminant;
    mixing a slipstream with a portion of the process stream to form an aqueous stream having a water concentration of greater than 50 wt. %,
    contacting the aqueous stream with an exchange resin; and
    withdrawing a purified process stream from the exchange resin, wherein the purified process stream comprises a reduced amine content.

2. The process of claim 1, wherein the slipstream comprises methanol, water, methyl acetate, acetic acid, and mixtures thereof.

3. The process of claim 1, wherein the slipstream comprises less than 20 wt. % of acetic acid.

4. The process of claim 1, wherein the purified process stream comprises less than 1 wppm amine, based on total weight of the purified process stream.

5. The process of claim 1, wherein the purified process stream further comprises a reduced corrosion metal content.

6. The process of claim 1, wherein the at least one amine compound comprises an iodine salt.

7. The process of claim 1, wherein the molar ratio of nitrogen in the amine compound to metal in the corrosion metal contaminants is greater than 3:1.

8. The process of claim 1, further comprising:
    reacting carbon monoxide with at least one reactant in a reactor containing a reaction medium to produce a reaction solution comprising acetic acid, wherein the at least one reactant is selected from the group consisting of methanol, methyl acetate, methyl formate, dimethyl ether and mixtures thereof, and wherein the reaction medium comprises water, acetic acid, methyl acetate, methyl iodide, and a catalyst; and
    withdrawing the reaction solution and flashing the reaction solution to yield a vapor crude product stream and the carbonylation process stream.

9. The process of claim 8, wherein the slipstream comprises a portion of the at least one reactant fed to the reactor.

10. The process of claim 8, further comprising:
    separating the vapor crude product stream to form a first overhead stream and a sidestream comprising acetic acid;
    condensing the overhead stream and biphasically separating the condensed overhead stream to form a light phase and heavy phase; and
    drying the sidestream to yield a second overhead stream comprising water and a residue comprising the dried acetic acid.

11. The process of claim 10, wherein the slipstream comprises a portion of the light phase.

12. The process of claim 10, wherein the slipstream comprises a portion of the heavy phase.

13. The process of claim 10, wherein the slipstream comprises a portion of the second overhead stream.

14. The process of claim 10, further comprising:
separating a portion of the light phase to yield a third overhead stream enriched in permanganate reducing compounds and a bottoms stream comprising methyl acetate and water; and
condensing and extracting third overhead stream to form a waste stream enriched in permanganate reducing compounds and a raffinate comprising methyl iodide.

15. The process of claim 14, wherein the slipstream comprises a portion of the bottoms stream.

16. The process of claim 14, wherein the slipstream comprises a portion of the raffinate.

17. A process for removing amine compounds in a carbonylation process, the process comprising the steps of:
contacting at least one reactant composition, comprising (i) a reactant selected from the group consisting of methanol, methyl acetate, methyl formate, dimethyl ether and mixtures thereof and (ii) an amine, with an exchange resin to produce a purified reactant feed stream having a reduced amine content;
reacting carbon monoxide with the purified reactant feed stream in a reactor containing a reaction medium to produce a reaction solution comprising acetic acid, and wherein the reaction medium comprises water, acetic acid, methyl acetate, methyl iodide, and a catalyst; and
withdrawing a reaction solution from the reactor, wherein the reaction solution is substantially free of amine compounds.

18. The process of claim 17, wherein the at least one reactant comprises amine compounds in an amount of at less than 100 wppm.

19. The process of claim 17, wherein the purified reactant feed stream comprises less than 1 wppm amine, based on total weight of the purified reactant feed stream.

20. The process of claim 17, further comprising:
flashing the reaction solution to yield a vapor crude product stream and the carbonylation process stream;
contacting the carbonylation process stream with an exchange resin; and
withdrawing a purified process stream from the exchange resin, wherein the purified process stream comprises a reduced corrosion metal contaminants.

* * * * *